(12) United States Patent
Scheins (10) Patent No.: US 8,080,799 B2
(45) Date of Patent: Dec. 20, 2011

(54) METHOD FOR POSITRON EMISSION TOMOGRAPHY AND PET SCANNER

(75) Inventor: Juergen Johann Scheins, Aldenhoven (DE)

(73) Assignee: Forschungszentrum Juelich GmbH, Juelich (DE)

( * ) Notice: Subject to any disclaimer, the term of this patent is extended or adjusted under 35 U.S.C. 154(b) by 0 days.

(21) Appl. No.: 12/734,060

(22) PCT Filed: Oct. 16, 2008

(86) PCT No.: PCT/DE2008/001699
§ 371 (c)(1),
(2), (4) Date: Apr. 8, 2010

(87) PCT Pub. No.: WO2009/056094
PCT Pub. Date: May 7, 2009

(65) Prior Publication Data
US 2010/0230602 A1    Sep. 16, 2010

(30) Foreign Application Priority Data

Oct. 30, 2007  (DE) .................. 10 2007 052 035

(51) Int. Cl.
*G01T 1/10*   (2006.01)
(52) U.S. Cl. ..................................... 250/362
(58) Field of Classification Search ........... 250/362, 250/363.01–363.1, 370.01–370.15
See application file for complete search history.

(56) References Cited

U.S. PATENT DOCUMENTS

| | | | |
|---|---|---|---|
| 6,804,325 B1 | 10/2004 | Smith | |
| 2003/0001098 A1* | 1/2003 | Stoddart et al. | 250/363.04 |
| 2005/0151084 A1 | 7/2005 | Zibulevsky et al. | |
| 2009/0124900 A1* | 5/2009 | Vandenberghe | 600/436 |

OTHER PUBLICATIONS

Wan et al., "Probability based positron range modeling in inhomogeneous medium for PET,", 2006, IEEE Nuclear Science Symposium Conference Record, pp. 3372-3375.*

Mark F Smith et al: "Analysis of Factors Affecting Positron Emission Mammography (PEM) Image Formation" IEEE Transactions on Nuclear Science, IEEE Service Center, New York, NY, US, Bd. 50, Nr. 1, Feb. 1, 2003, XP011077994 Zusammenfassung; Abbildungen Seite 53, rechte Spalte, Zeile 36—Zeile 39.

K. Ziemons, et al.: "The ClearPET™ project: development of a 2nd generation high-performance small animal PET scanner", Nuclear Instruments and Methods in Physics Research, Section A, 537, (2005), pp. 307-311.

C. Labbe, et al.: An object-oriented library incorporating efficient projection/backprojection operators for volume reconstruction in 3D PET, Proc. of 3D99 Conference, 1999, Egmond aan Zee, Netherlands.

* cited by examiner

Primary Examiner — Kiho Kim
(74) Attorney, Agent, or Firm — Jordan and Hamburg LLP (57) ABSTRACT

Disclosed is a method for positron emission tomography and to a PET scanner. The positron emission tomography method employs the following steps: a) two photons are emitted in opposite directions by an annihilation event in the sample, b) at least two of a plurality of detectors arranged around the sample are prompted to output a signal by the two photons, c) a signal line on which the event may have taken place is determined from the location of the detectors which have output a signal, d) this signal line is evaluated in the tomographic reconstruction of the sample, wherein for each event a plurality of signal lines are determined and evaluated in the tomographic reconstruction of the sample. As described at the outset, the reconstructed image thus becomes more accurate and noise is reduced. The method and the apparatus can improve the signal-to-noise ratio of images.

18 Claims, 6 Drawing Sheets

METHOD FOR POSITRON EMISSION TOMOGRAPHY AND PET SCANNER

The invention relates to a method for positron emission tomography and to a PET scanner.

Positron emission tomography (PET) employs scintillation detectors, which detect the photons emitted in pairs in opposite directions during the annihilation of electron-positron pairs in the sample.

BACKGROUND OF THE INVENTION

In a PET measurement, the key is to detect the annihilation of electron-positron pairs in the sample and to localize the signal line on which the respective event has taken place. Based on a plurality of such events, it is then possible to determine the inner activity distribution of the sample using tomographic reconstruction.

During each event, two photons are emitted simultaneously in opposite directions, the spatial orientation thereof not being predictable, as this is isotropic. For this reason, a plurality of detectors are arranged around the sample in a PET scanner, thereby ensuring that each of the two photons resulting from an event strikes a detector. If two of the detectors, which generally are scintillation crystals having PMTs (photomultiplier tubes) or APDs (avalanche photodiodes), register an event simultaneously, which is monitored by a coincidence circuit, information is obtained to the effect that an event took place on a connecting line between the two detectors. This line is referred to as the signal line or line of response (LOR).

Previously, the measured coincidences of individual crystal combinations were associated with a certain signal line. Typically, a signal line is established by connecting a select central or representative point in the two crystals involved.

The disadvantage is that noise, and frequently also artifacts, are present in the recorded data. These interferences are decisively amplified by the tomographic reconstruction, which is equivalent to solving an inverse problem, and reduce the quality of the image that is ultimately obtained from the reconstruction.

SUMMARY OF THE INVENTION

It is therefore the object of the invention to provide a method for positron emission tomography and a PET scanner employing this method, which supply more accurate tomographic reconstructions than is possible according to the state of the art.

These objects are achieved according to the invention by a method according to the main claim and by apparatuses for performing this method according to additional independent claims.

Starting from the preamble of claim 1, the object is achieved according to the invention by the characteristics provided in the characterizing part of claim 1.

It was found that the actual information content of a detected coincidence was spatially "blurred" due to the measurement process, and is not represented, or cannot be depicted, by a single signal line: If two spatially extended detectors register a coincidence, the associated event cannot be unequivocally associated with a certain single signal line (LOR). Rather, due to the finite extension or resolution, the detector combination observes an entire bundle of signal lines or LORs in the 3D space, which therefore represent all possible candidates of the causal signal line. Furthermore, the detection probability of each signal line of a bundle is not necessarily uniform due to geometric effects. It remains unknown which of these signal lines in the bundle in fact triggered the registration, which is to say all LORs in the bundle are possible sources for the signal according to the detection probability thereof. The structure of the signal line bundles varies according to the sizes, positions, and orientations of the two respectively observed detectors. Accordingly, the true information about the location of the event supplied by the simultaneous response of two particular detectors is represented by such a bundle of signal lines between the two detectors, and the contributions of the individual signal lines can have different weightings.

Furthermore, additional measuring inaccuracies and additional blurring of the measurement information are caused by Compton scattering of the photons inside the crystals and the statistically fluctuating signals of both the scintillation light and the downstream electronics, which is to say that crystals adjacent to the actual crystal are erroneously detected as the origin of the coincidence.

This blurring of the measurement information in the signal line space is not adequately taken into consideration in the project space according to the prior art. This must be distinguished from a consideration or modeling of the blurring within the context of a reconstruction algorithm with the objective of improving the resolution of the resulting images. This would be a known and common method. In contrast, the method according to the invention edits the projection data used in an improved manner prior to employing a reconstruction method. The procedural step of modeling the blurring or resolution directly in the reconstruction method is independent of the invention and is conducted thereafter. The prior art is based on a simplified, idealized detection model for interpolation or editing to obtain tomographically usable projection data.

When using the method according to the invention and the apparatuses for performing the method, for the first time detector crystal sizes and the general system resolution can be taken into consideration in the definition of the projection data for the reconstruction. In this way, smoothed projection data can now be made available, without reducing the actual resolution of the scanner system for the image reconstruction, resulting in images having an improved signal-to-noise ratio and therefore better image quality.

Advantageous refinements of the invention will be apparent from the dependent claims.

The figures show schematic illustrations and image results obtained from data using the method according to the invention.

DESCRIPTION OF THE PREFERRED EMBODIMENTS

Figure 1:
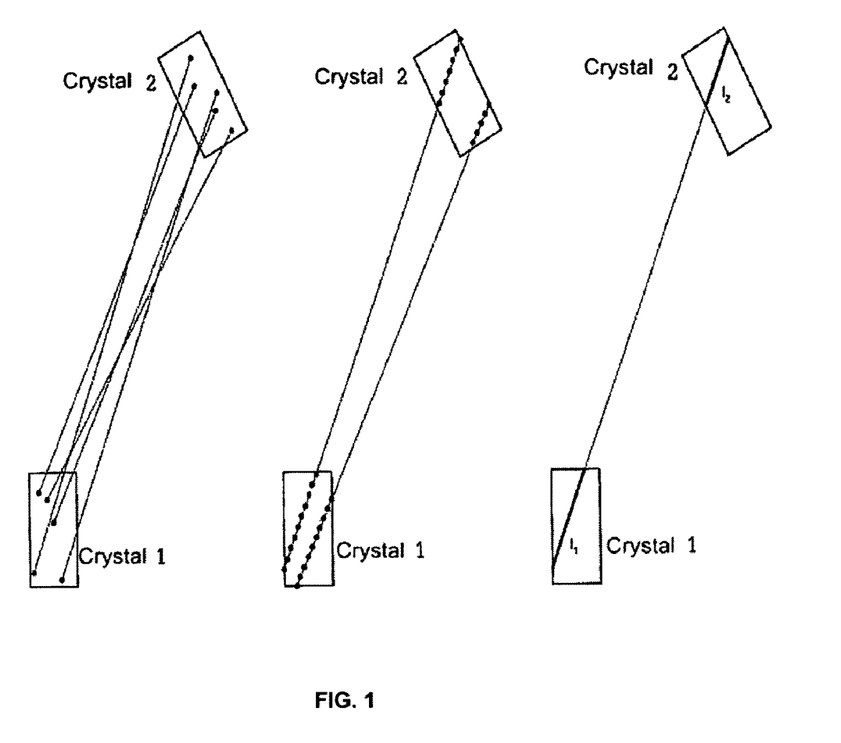
FIG. 1 shows detection location combinations in crystals.

FIG. 1 shows a sampling of a crystal combination comprising two different crystals by way of example in a 2D representation according to two embodiments of the method according to the invention.

Embodiment 1: (left) individual, randomly determined points in both crystals in each case define an observed signal line, (center) different combinations of certain points form the same signal line.

Embodiment 2: (right) the effective weighting of a signal line (LOR) results from the product of $p_{12}=I_1*I_2$ of the intersecting lengths of this LOR with the crystals involved.

Figure 2:
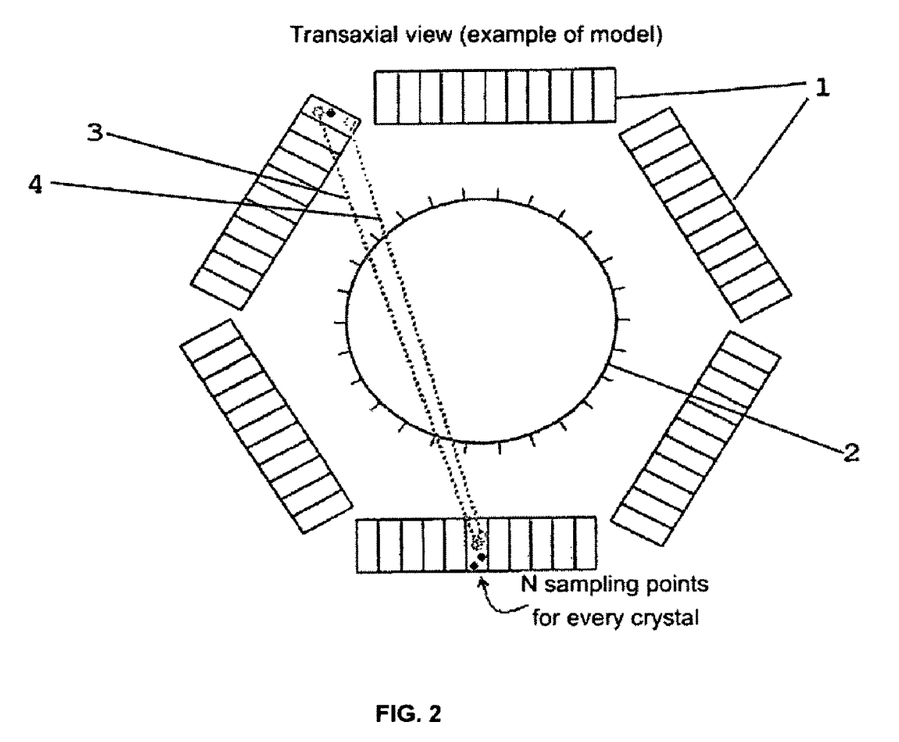
FIG. 2 is an illustration of a typical detector topology.

FIG. 2 shows a transaxial view of an irregular detector topology 1 (outer part) and a virtual regular cylinder detector 2 (VRZ, inner part). The VRZ is used in the embodiment of the method according to the invention in which the points of intersection of each signal line to be considered for this reconstruction are determined by way of the VRZ and are treated in the reconstruction as if detectors had been present there. Each physical signal line 3, 4 (LOR) intersects the cylinder in exactly two unequivocal points. For the association of the points of intersection, the cylinder is segmented into a finite number of partial surfaces (virtual detectors) by introducing cylinder rings and regular ring subsets. Each point of intersection of the LOR with the cylinder is located on a unequivocally determined partial surface, so that, in each case, the tube of response (TOR) spanned by the cut partial surfaces includes the LOR to be associated. In this way, each physical signal is unequivocally associated with a corresponding TOR.

Figure 3:
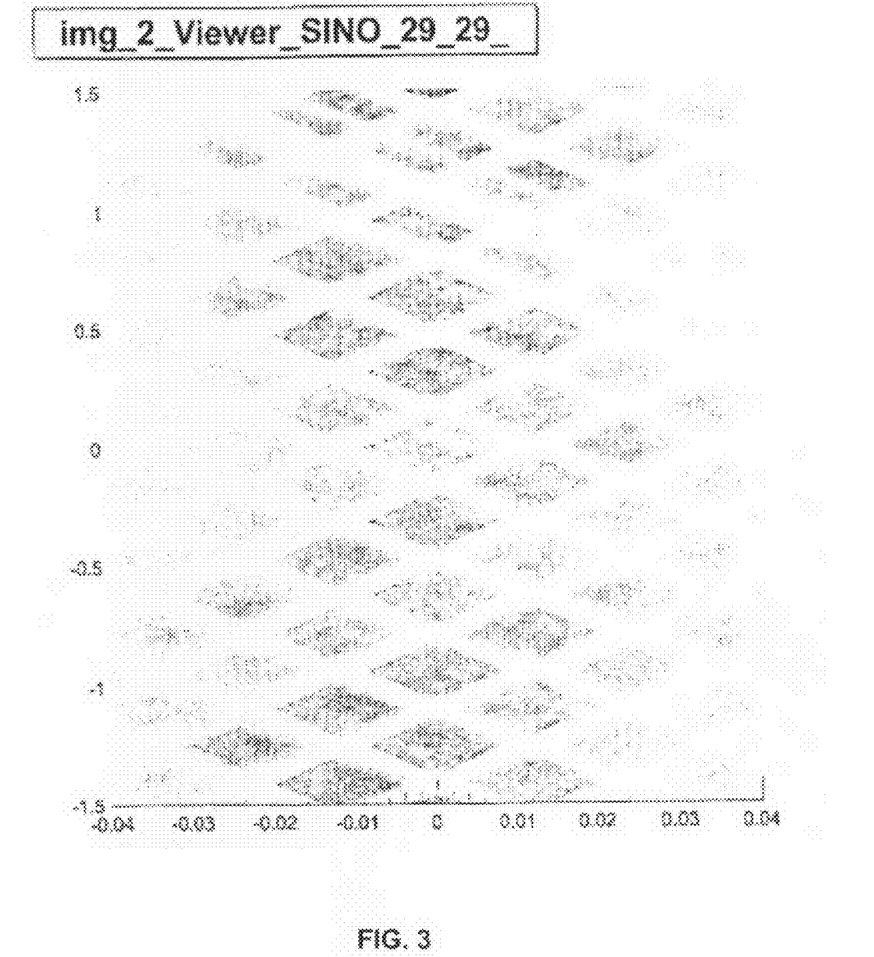
FIG. 3 shows a projection data histogram.

FIG. 3 shows a projection data histogram (directional angle on the Y-axis, radial coordinate on the X-axis) for a certain cylinder ring of the VRZ model; the measured coincidence data originate from a homogeneous activity-filled cylinder and were recorded with the ClearPET Neuro PET scanner (rotating detectors) and converted without further corrections to the VRZ model using a precalculated distribution key. The sensitivity gaps due to transaxial detector gaps are clearly visible. With increases to the radial coordinate, the geometrical information is blurred due to the "depth-of-interaction" effect and corresponds to a worsening of the resolution according to the underlying geometric properties. Resolution losses, due to "depth of interaction," with increasing radial distances are causally related to the increasing inclination of the crystals with respect to the LORs involved. It is therefore exclusively a geometric effect. Due to the inclination, the effective size of the respective crystals appears enlarged in the radial direction, because the crystal lengths are typically larger than the width or length of the crystal surface (typical block design) in order to increase sensitivity. This projected effective crystal cross-section reduces the radial spatial resolution accordingly. This blurring of the projection data becomes visible by way of the method according to the invention.

Figure 4:
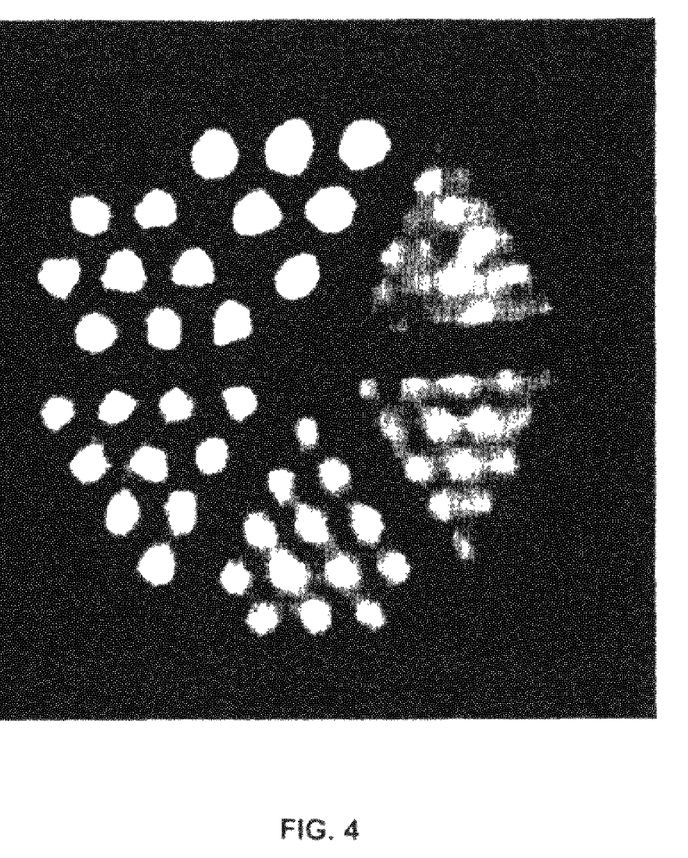
FIG. 4 shows a transaxial layer of a reconstructed image computed from projection data generated according to the invention.

FIG. 4 shows a transaxial layer of a reconstructed image of the mini-Derenzo phantom, measured with the ClearPET Neuro scanner; the measurement data was converted into the VRZ model with high granularity using a geometric probability distribution according to the invention and was subsequently iteratively reconstructed within the scope of the VRZ model. The axially oriented, activity-filled capillaries have diameters of 2 mm (top), 1.8 mm, 1.6 mm (left), 1.4 mm (bottom), 1.2 mm, and 1.0 mm (right). The 1.2 mm structures can still be clearly distinguished. The mini-Derenzo phantom overall has an active radial diameter of approximately 30 mm.

Figure 5:
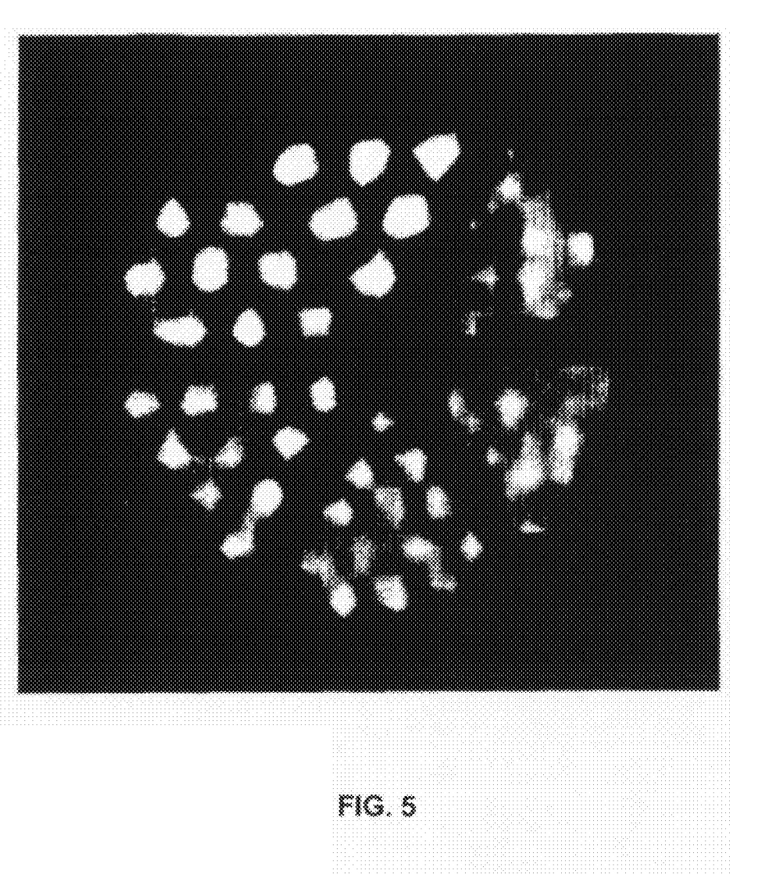
FIG. 5 shows a transaxial layer of a reconstructed image generated from projection data obtained from raw detector data according to the prior art.

FIG. 5 shows the same transaxial layer as in FIG. 4 using identical underlying measurement data as in FIG. 4; however, the acquired projection data was not converted using a distribution key according to the invention. The iterative reconstruction was carried out with a sinogram-based program [2] using projection data according to the prior art. The contrast-to-noise ratio is clearly worse than in FIG. 4. Structures smaller than 1.4 mm can no longer be distinguished.

Figure 6A:
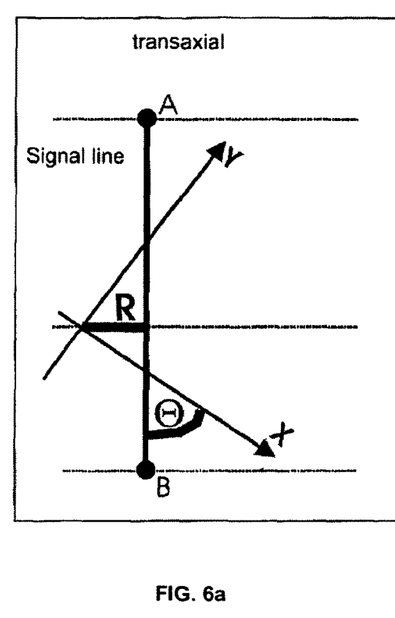
FIGS. 6a and 6b show a geographical representation of the unequivocal characterization of the position of a signal line in the three-dimensional space.
Figure 6B:
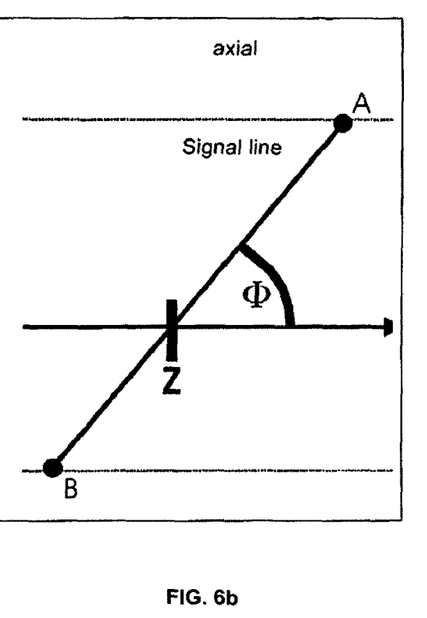

FIGS. 6a and 6b show the parameters required for the unequivocal characterization of the position of the signal line, such as are used for the definition of projection values according to Formula 1. In the figures, points A and B are points located on the signal line. FIG. 6a shows the projection angle Θ located in the transaxial plane (xy plane) and the radial displacement R. FIG. 6b shows the axial displacement Z along the axial direction (Z-axis) of a detector tube and the angle of inclination Φ of the signal line with respect to the xy plane.

The invention will be explained hereinafter in general terms.

According to the invention, the positron emission tomography method employs the following steps:

a) two photons are emitted in opposite directions by an annihilation event in the sample, b) at least two of a plurality of detectors arranged around the sample are prompted to output a signal by the two photons, c) a signal line on which the event may have taken place is determined from the location of the detectors which have output a signal, d) this signal line is evaluated in the tomographic reconstruction of the sample, wherein for each event a plurality of signal lines are determined and evaluated in the tomographic reconstruction of the sample.

As described at the outset, the reconstructed image thus becomes more accurate and noise is reduced.

A signal line as defined by the invention is a line connecting two different points in the three-dimensional space, each of the two points describing a local detection location of a photon from the annihilation process.

Any arbitrary signal line can be unequivocally characterized by exactly four parameters (Θ, R, Φ, Z)

two in the transaxial plane (xy plane):

a projection angle Θ; and a radial displacement R and two in the axial direction:

an axial displacement Z (along the Z-coordinate axis orthogonal to the xy plane); and an angle of inclination Φ of the signal line with respect to the xy plane.

If S (Θ, R, Φ, Z) is the signal of a signal line as a function of the four parameters, then a projection value $P_i$ is a four-dimensional integral over a specific four-dimensional partial volume $V_i$ as follows.

$$P_i = \int\int\int_{Vi}\int S(\Theta, R, \Phi, Z) d\Theta dR d\Phi dZ \quad \text{Formula (1)}$$

Projection data as defined in the invention shall be understood as a quantity of distinguishable projection values $P_i$ resulting from the integration according to Formula 1 having different specific 4D partial volumes $V_i$.

A plurality of signal lines shall be understood as at least 2, and preferably more, such as at least 10, 100, 1000, 10,0000 or 1,000,000.

Preferably every possible signal line for every detector combination is weighted in the evaluation with a probability distribution which is a measure of the event having occurred with which probability on which signal line. As a result of the weighting using a probability function, the projection data corresponds better to the true physical information content produced by the event.

In an advantageous embodiment of the invention, the probability distribution can be determined by way of a Monte Carlo technique, wherein a plurality of locations located within the two detectors are randomly determined and signal lines between a location in the one detector and a location in the other detector are considered signal lines on which the event may have taken place. In this case, it can be stated or summarized by a distribution key, which according to Formula (2) is described by $$S_{jk}=N_{jk}/N_{tot,j}. \quad (2)$$

Where:

$N_{tot,j}$: is the number of signal lines generated from a randomly selected point in each crystal for the crystal combination j k is a certain TOR produced $N_{jk}$: is the number of LORs generated which are located in the TOR k.

In a further embodiment of the invention, the probability distribution is determined such that, for a plurality of signal lines intersecting the two detectors, the intersecting lengths are determined, at which they intersect the detectors.

For this purpose, the product of the lengths of a signal line can be considered a measure of the probability of the event having taken place on this line. In this procedure, the probability distribution can be determined more quickly than through the random determination of a plurality of locations inside the two detectors.

In the evaluation of the measurement information, the location dependence of the sensitivity is advantageously taken into consideration. The location dependence is described by the probability distribution. By taking the location dependence of the sensitivity of the detector pairs into consideration, it is possible to generate projection data which comes closer to the true information content of the detected radiation, thereby improving the contrast-to-noise ratio of the reconstructed images. In the determination of the projection data, it is also possible to consider detector-specific properties, such as interferences, inhomogeneities, or detector gaps. Detector-specific distortions of the projection data generated are minimized or avoided entirely.

For the generation of probability distributions, it is also possible to conduct detector simulations, which simulate Compton scattering in the crystals, for example. In the typical block design of the scintillation crystals, Compton scattering and inaccuracies in terms of metrology produce misdetections of crystals, which is to say incorrect LOR localizations occur which cause a worsening of the location information beyond geometry. These additional information losses can likewise be taken into consideration. These effects, however, are more complex and can only be quantified by accordingly complex simulations or measurements.

By simulating the physical processes in the detectors by way of particle trace tracking using the Monte Carlo technique in the detector medium, in the manner of the simulation programs which are described in the publication of S. Agostinelli et al, "GEANT-A Simulation toolkit", Nucl. Instr. Methods Phys. Res. A 506 (2003), pgs. 250-303, detailed determination of the detector resolution or information blurring is possible. The information gained can be used to determine a more accurate distribution key, which describes not only the crystal sizes but also the crosstalk behavior of the signals in adjacent crystals. In addition to the simulation, targeted measurements of the detector response can be used analogously and can optionally replace simulations.

In a particularly advantageous embodiment of the method according to the invention, prior to tomographic reconstruction, the points of intersection of each signal line (LOR) to be considered for this reconstruction are determined by way of a specified geometric shape and treated in the reconstruction as if detectors had been present there. To this end, the geometric shape is preferably discretized in a finite number of partial surfaces for determining the points of intersection. It is also preferable to select a circle or a cylinder as the geometric shape.

It was recognized that, when employing this procedure, the symmetry of the geometric shape can advantageously be used to simplify the tomographic reconstruction. The higher the number of symmetries for the geometric shape, the lower the complexity required for the geometric calculation within the scope of the reconstruction method. The reduced complexity results in shorter computation times for image reconstruction.

This embodiment of the method according to the invention also enables a separation between the detector geometry description and optimizable reconstruction algorithms for image reconstruction. The reconstruction algorithm must only be optimized for a single geometry, which has the symmetries advantageous for an optimal computation speed. However, the geometry of the physically present scanner is so designed, that the data recorded with it can always be projected onto this one advantageous shape, as the points of intersection of the signal lines or TORs to be considered for this reconstruction are determined by way of this geometric shape. Thus, images can be reconstructed more quickly.

The invention further relates to an apparatus, and particularly a positron emission tomography scanner, which is suited to carrying out the method according to the invention and either comprises means for determining the probability distribution, or means for providing the probability that an event registered by at least two detectors has taken place on a particular signal line between the two detectors.

For example, according to alternative 2, a positron emission tomography scanner can be equipped with data storage media on which the LOR probability distributions for detector pairs are stored in the form of look-up tables. If two detectors respond simultaneously, such look-up tables can be called upon to determine on which signal lines between the two detectors the event has taken place with what probabilities. These look-up tables are valid as long as the geometry of the scanner remains unchanged and the granularity of the virtual cylinder does not change.

However, the scanner according to alternative 1 may also comprise means for determining the probability distribution. A means for determining the probability distribution shall be understood, for example, as a computer which applies the methods according to the invention. This variant is advantageous, for example, when the mechanical design of the scanner is such that the geometry thereof can be varied, for example, so that it can be adjusted to samples or patients having different sizes.

According to the invention, a probability distribution L (LORi|crystal combination j), from which a distribution key or distribution of the information among several virtual TORs can be derived, is determined for the location information supplied by the detector. This distribution key can be determined individually, prior to each measurement, or once before starting up the scanner, and can form the basis for all further measurements. The invention therefore relates to an imaging method, which is based on projection data generated with the distribution key, and to a PET scanner, the raw data measured therewith being processed using the distribution key.

The application of a spatially continuously variable distribution key, which is included in the subject matter of this invention, in principle prevents inhomogeneities in the projection space and results in a significant improvement of the contrast-to-noise ratio. The basic concept is the generation of an improved scanner-specific probability distribution L (LORi|crystal combination j), from which such a distribution key can be directly derived. The physical crystal sizes can be taken into consideration in a simplified manner by employing a geometric Monte Carlo method. For this purpose, in each of the two crystals of a specific 3D crystal combination j, a point is independently randomly sampled, and these two points together define a representative 3D LOR, which is likewise part of the LOR bundle of the crystal combination (FIG. 1 left). The underlying assumption of this approach is that a gamma quantum can cause a detectable interaction with homogeneous probability throughout the entire crystal. In this way, a 3D LOR bundle can be generated for any arbitrary crystal combination, with the statistical precision thereof being dependent only on the randomly sampled point density distribution. In the process, all the LORs observed occur in at characteristic frequency, because different point combinations can represent the same LOR i (FIG. 1 center). This frequency distribution density of the LORs i for a crystal combination j corresponds to the probability distribution L (LOR i|crystal combination j) that is sought. This distribution can be used to distribute the measurement data in sinograms/histograms over different projection bins. An optimal use of the invention is provided by the VRZ concept, for which all the LORs generated are unequivocally projected onto a regular cylinder. The virtual division on the cylinder segments the projection space first into individual virtual 3D tubes (tubes of response, TOR), for which the reconstruction provides suitable projectors. Each virtual TOR defines a specific unique 3D LOR bundle and each LOR that is generated can be precisely associated with such a TOR, which is to say a LOR bundle (FIG. 2). This produces a compact distribution key, which establishes the contribution of a crystal combination j to each virtual TOR k. If $N_{tot,j}$ is the number of LORs generated for the crystal combination j, and k is a certain TOR and $N_{jk}$ is the number of LORs generated and located in the bundle or the TOR k, then the resulting standardized (geometric) distribution key is:

$$S_{jk}=N_{jk}/N_{tot,j}. \quad (2)$$

Taking the detector geometry into consideration, this scanner-specific distribution key is calculated in advance, and every coincidence event that is detected is divided among the virtual TORs according to this key, while preserving the total number of events. The efficient calculation and application of this distribution key in the projection space prior to the actual iterative construction is the subject matter of this invention.

Another subject matter of this invention is a method for the accelerated calculation of the distribution key on the basis of the crystal geometries according to equation (2). The numerical accuracy that is achieved by the Monte Carlo method is highly dependent on the randomly sampled and evaluated number of LORs for each crystal combination, so that a satisfactory accuracy is only achieved with very high point densities, and thus very long computing times. Instead, a semi-analytical integral method can be implemented. Due to the geometry, the weighting with which a certain LOR occurs is proportional to the product of the resulting intersecting lengths of the respective LOR with the two crystals (FIG. 1 right). The two intersecting lengths $l_1$ and $l_2$ (3D radon transform for a certain 3D signal line of the two functions $f_{1,2}(x,y,z)=1$, if (x,y,z) is present in crystal 1 or 2, otherwise $f_{1,2}(x,y,z)=0$) can be calculated for any arbitrary LOR, and the product $p_{12}=l_1*l_2$ results in the relative effective contribution weight. In this way, all point combinations captured by the LOR observed are taken into consideration at the same time. The quantity of the LORs to be observed is significantly less than for the above Monte Carlo method, while achieving the same accuracy, and therefore reduces the computing complexity. In order to preserve the total number of events, the distribution keys for each individual crystal combination j are standardized to one. Within the context of statistic accuracy as a function of the number of evaluated LORs, both methods result in equivalent distribution keys, which is to say the weightings $S_{jk}$ converge for high LOR sampling into the same values.

The primarily proposed Monte Carlo method requires higher computing complexity, but offers greater flexibility in modeling the detection probabilities, provided they are not homogenous in the crystals involved. Location-dependent detection probabilities can thus likewise be simulated by introducing weighted points. This constitutes another improvement of the probability modeling of the location information. In this way, points in the vicinity of the crystal surfaces, for example, can have a lower detection probability and are considered with accordingly smaller local weightings.

Another characteristic of the invention is that accurate detector simulations (such as by way of GEANT) can be used for generating a probability distribution, which then correctly simulates all physical effects in the detection process, such as Compton scattering in the crystals. In this way, distribution keys having a very accurate description of the system can be incorporated and implemented. The combination of dedicated detector simulations with the distribution keys and the VRZ concept opens up possibilities for a very accurate yet nonetheless fast 3D PET reconstruction. While GEANT-based simulations are very time-consuming, they can be conducted once so as to allow the determination of a very precise distribution key. As a result, the duration of the simulations has no further influence on the required reconstruction times. Until now, the use of precise detector simulations has not been suitable for a routine application.

Moreover, by using a scanner-specific distribution key, general reconstruction programs (such as the VRZ model) can be implemented and optimized, which no longer have to be individually adapted to different scanners, with regard to the software. The scanner geometry and data conversion is included exclusively in the respective distribution key, and thus, as compared to the prior art, greater flexibility and portability for different scanner systems is achieved.

The method according to the invention can be applied, for example, to the ClearPET Neuro Small Animal PET scanner [1]. This scanner comprises detector blocks having 8×8 crystals in two crystal layers disposed behind one another and made of different crystal materials. The crystal size is 2×2×10 mm. In each case, four such detector blocks are disposed axially in what is referred to as a cassette. The complete detector system is equipped with 20 of these cassettes in a ring shape, amounting to a total of 10240 crystals. The special characteristic is that the entire system rotates axially around the measurement object during data acquisition in order to be able to fill some of the existing gaps in the projection space, resulting from detector gaps. The rotation is carried out in 1-degree angular intervals, so that coincidences can be measured in a stationary manner in each individual detector position.

The PET data measured in 3D with the ClearPET Neuro system is converted to the VRZ model having a selected high granularity using a geometric distribution key, which models the crystal sizes. The stationary distribution key is used equally for each detector position. The resulting partial data can then be rotated accordingly, loss-free, within the scope of the VRZ model and is then added to form a total data record. The distribution key was calculated with high accuracy using the semi-analytical integral method described. FIG. 3 shows, by way of example, a projection data histogram of an individual ring level, which was calculated using the distribution key from the measurement of an activity-filled homogeneous cylinder phantom. The individual rhombic data segments correspond to the individual virtual TORs (see above), which are respectively linked to the individual projectors in the reconstruction. The gray tones correspond to the associated channel intensity or the effective projection measurement value. The sensitivity gaps due to transaxial detector gaps are clearly visible. With increases to the radial coordinate, the geometrical structures are blurred, due to the expected "depth-of-interaction" effect, corresponding to degraded resolution according to the underlying probability distribution, as it actually exists in the scanner.

For the VRZ model, an iterative complete 3D reconstruction exists. The converted projection data can be directly reconstructed into a 3D image within the context of this formalism (FIG. 4). The mini-Derenzo phantom used comprises capillary structures having different capillary diameters (2.0 mm, 1.8 mm, 1.6 mm, 1.4 mm, 1.2 mm, 1.0 mm) and was axially oriented for the measurement. The figure shows a transaxial section through the capillaries. The capillary structures are very clearly apparent down to 1.2 mm. Compared to this, FIG. 5 shows a reconstruction of the same measurement data, based on the prior art, using sinograms by way of [2] without this invention. The difference in the contrast-to-noise ratio is obvious. The 1.2 mm structures can no longer be distinguished here. The use of a precise distribution key results in a significant improvement in the image quality.

[1] K. Ziemons et al., The Clear PET project: Development of a 2nd generation high-performance small animal PET Scanner, Nucl. Instr. Meth A 537, 2005, pp.307-311

[2] C. Labbe, K. Thielemans, H. Zaidi, C. Morel, An object-oriented library incorporating efficient projection/backprojection operators for volume reconstruction in 3D PET, Proc. of 3D99 Conference, 1999, Egmond aan Zee, Netherlands

The invention claimed is:

1. A method for positron emission tomography, comprising the following steps: a) two photons are emitted in opposite directions by an annihilation event in a sample; b) at least two of a plurality of detectors arranged around the sample are prompted to output a signal by the two photons; c) a signal line on which the event may have taken place is determined from the location of the detectors which have output a signal; and d) this signal line is evaluated in the tomographic reconstruction of the sample, wherein prior to the tomographic reconstruction of the sample, for each event a plurality of signal lines are determined, the plurality of signal lines then being evaluated in the tomographic reconstruction of the sample.

2. A method for positron emission tomography, comprising the following steps: a) two photons are emitted in opposite directions by an annihilation event in a sample; b) at least two of a plurality of detectors arranged around the sample are prompted to output a signal by the two photons; c) a signal line on which the event may have taken place is determined from the location of the detectors which have output a signal; and d) this signal line is evaluated in the tomographic reconstruction of the sample, wherein prior to the tomographic reconstruction of the sample, for each event a plurality of signal lines are determined and evaluated in the tomographic reconstruction of the sample; and wherein each signal line is weighted in the evaluation with a probability distribution which is a measure of the event having occurred with which probability on which signal line.

3. A method according to claim 2, wherein the probability distribution is determined such that a plurality of locations located within the two detectors are randomly determined and signal lines between a location in the one detector and a location in the other detector are considered to be lines on which the event may have taken place.

4. A method according to claim 2, wherein the probability distribution is determined such that, for a plurality of signal lines intersecting the two detectors the lengths are determined at which they intersect the detectors.

5. A method according to claim 4, wherein the product of the lengths of a line is considered to be a measure of the probability that the event has taken place on this line.

6. A method according to claim 2, wherein detector simulations are conducted for generating the probability distributions.

7. A method according to claim 6, wherein the Monte Carlo method is employed for the detector simulation.

8. An apparatus for performing the method according to claim 2, wherein means are provided for determining probability distribution.

9. An apparatus for performing the method according to claim 2, comprising means for providing the probability that an event recorded by at least two detectors has taken place on a particular signal line between the two detectors.

10. A method according to claim 2, wherein measurements of the detector behavior are used for generating the probability distributions.

11. A method for positron emission tomography, comprising the following steps: a) two photons are emitted in opposite directions by an annihilation event in a sample; b) at least two of a plurality of detectors arranged around the sample are prompted to output a signal by the two photons; c) a signal line on which the event may have taken place is determined from the location of the detectors which have output a signal; and d) this signal line is evaluated in the tomographic reconstruction of the sample, wherein prior to the tomographic reconstruction of the sample, for each event a plurality of signal lines are determined and evaluated in the tomographic reconstruction of the sample; and, wherein at least one detector is taken into consideration in the evaluation of the location dependence of the sensitivity.

12. A method according to claim 11, wherein the location dependence is already taken into consideration in the determination of the probability distribution.

13. A method for positron emission tomography, comprising the following steps: a) two photons are emitted in opposite directions by an annihilation event in a sample; b) at least two of a plurality of detectors arranged around the sample are prompted to output a signal by the two photons; c) a signal line on which the event may have taken place is determined from the location of the detectors which have output a signal; and d) this signal line is evaluated in the tomographic reconstruction of the sample, wherein prior to the tomographic reconstruction of the sample, for each event a plurality of signal lines are determined and evaluated in the tomographic reconstruction of the sample; and wherein the weighted signal lines are transferred into one or more sinograms prior to the tomographic reconstruction.

14. A method for positron emission tomography, comprising the following steps: a) two photons are emitted in opposite directions by an annihilation event in a sample; b) at least two of a plurality of detectors arranged around the sample are prompted to output a signal by the two photons; c) a signal line on which the event may have taken place is determined from the location of the detectors which have output a signal; and d) this signal line is evaluated in the tomographic reconstruction of the sample, wherein prior to the tomographic reconstruction of the sample, for each event a plurality of signal lines are determined and evaluated in the tomographic reconstruction of the sample; and wherein prior to the tomographic reconstruction, the points of intersection of each signal line to be considered for this reconstruction are determined by way of a specified geometric shape and are treated in the reconstruction as if detectors had been present there.

15. A method according to claim 14, wherein the geometric shape is discretized for a finite number of intervals for determining the points of intersection.

16. A method according to claim 14, wherein a circle is selected as the geometric shape.

17. A method according to claim 14, wherein a cylinder is selected as the geometric shape.

18. A method for positron emission tomography, comprising the following steps:

two photons are emitted in opposite directions by an annihilation event in a sample;

at least two of a plurality of detectors arranged around the sample are prompted to output a signal by the two photons;

a first signal line on which the event may have taken place is determined from the location of the detectors which have output a signal;

evaluating said first signal line prior to tomographic reconstruction, said evaluation comprising for each said event, after said signal line is determined: determining a plurality of second signal lines using projection space of recorded measurement data, and evaluating said plurality of second signal lines; and performing, after said first signal line evaluating, tomographic reconstruction using a physical model of an imaging process, said physical model being distinct from said projection space.

* * * * *